(12) United States Patent
Rosenberger et al.

(10) Patent No.: US 8,738,642 B2
(45) Date of Patent: May 27, 2014

(54) CLINICAL DATA MONITORING

(75) Inventors: Bryan Rosenberger, Pennsburg, PA (US); Timothy Eggena, Hamilton, GA (US); Robert Nary, Voorhees, NJ (US); Robert Hale, Atlanta, GA (US); Patrick Cline, Southlake, TX (US); Robert Ellis, Ocean Grove, NJ (US)

(73) Assignee: QSI Management, LLC, Irvine, CA (US)

( * ) Notice: Subject to any disclaimer, the term of this patent is extended or adjusted under 35 U.S.C. 154(b) by 554 days.

(21) Appl. No.: 12/438,085

(22) PCT Filed: Aug. 29, 2007

(86) PCT No.: PCT/US2007/019058
§ 371 (c)(1),
(2), (4) Date: Dec. 1, 2009

(87) PCT Pub. No.: WO2008/027461
PCT Pub. Date: Mar. 6, 2008

(65) Prior Publication Data
US 2010/0169355 A1    Jul. 1, 2010

Related U.S. Application Data

(60) Provisional application No. 60/823,785, filed on Aug. 29, 2006.

(51) Int. Cl.
*G06F 17/30*    (2006.01)
(52) U.S. Cl.
USPC .......................................................... 707/766

(58) Field of Classification Search
CPC .................................................. G06F 17/30395
USPC ................. 707/766, 706, 767, 722, 751, 765, 707/E17.074
See application file for complete search history.

(56) References Cited

U.S. PATENT DOCUMENTS

| | | | | |
|---|---|---|---|---|
| 6,151,581 A * | 11/2000 | Kraftson et al. | ................... | 705/3 |
| 6,766,368 B1 | 7/2004 | Jakobson et al. | | |
| 7,436,311 B2 * | 10/2008 | Rapaport et al. | ........... | 340/573.1 |
| 8,010,523 B2 * | 8/2011 | Djabarov | ....................... | 707/721 |
| 2004/0044292 A1 | 3/2004 | Yasushi et al. | | |
| 2004/0078211 A1 * | 4/2004 | Schramm-Apple et al. | ...... | 705/1 |
| 2004/0078224 A1 * | 4/2004 | Schramm-Apple et al. | ...... | 705/2 |

(Continued)

OTHER PUBLICATIONS

MicroStrategy 8™, Advanced Reporting Guide, Tenth Edition, Jul. 2005, version 8.0.1, published by MicroStrategy Incorporated.*

(Continued)

*Primary Examiner* — Hung T Vy
(74) *Attorney, Agent, or Firm* — Fish & Tsang, LLP

(57) ABSTRACT

Data is combined from multiple independent data stores, and is then queried using a data correlation engine. Contemplated engines preferably keep track of previously run correlations, and then makes those correlations available to clinicians for their own use. For example, a preferred system might provide a listing of correlations run by other clinicians in a particular medical specialty, or a particular community, whether geographic or otherwise. In another example, a preferred system might provide a listing of correlations sorted by popularity, so that the most frequently accessed correlations appear near the top of the list. In any case a clinician could simply view the list, and check off which correlations he/she would like to have run for his/her practice, or practice community.

15 Claims, 2 Drawing Sheets

(56) References Cited

U.S. PATENT DOCUMENTS

| | | | |
|---|---|---|---|
| 2004/0078225 A1* | 4/2004 | Schramm-Apple et al. | 705/2 |
| 2004/0243545 A1* | 12/2004 | Boone et al. | 707/2 |
| 2004/0267729 A1* | 12/2004 | Swaminathan et al. | 707/3 |
| 2005/0108216 A1* | 5/2005 | Schramm-Apple et al. | 707/3 |
| 2005/0240085 A1 | 10/2005 | Knoell et al. | |
| 2006/0111943 A1* | 5/2006 | Wu | 705/3 |
| 2006/0271561 A1* | 11/2006 | Schlachta-Fairchild et al. | 707/10 |
| 2007/0061393 A1* | 3/2007 | Moore | 709/201 |
| 2007/0106531 A1* | 5/2007 | Deakter | 705/2 |

OTHER PUBLICATIONS

MicroStrategy 8™, Advanced Reporting Guide, Tenth Edition, Jul. 2005, version 8.0.1, published by MicroStrategy Incorporated (pp. 185, 504, 520, 561).*

Markle Foundation a Public-Private Collaborative; Linking Health Care Information: Proposed Methods for Improving Care and Protecting Privacy; Feb. 2005.

* cited by examiner

CLINICAL DATA MONITORING

This application claims priority to U.S. provisional application Ser. No. 60/823,785, filed Aug. 29, 2006.

FIELD OF THE INVENTION

The field of the invention is data warehousing, and especially warehousing of patient demographic and clinical data.

BACKGROUND

There are numerous generic data warehousing solutions in the marketplace, including software from SAS™, Oracle™ and others. Those solutions could be adapted to ware-housing of patient demographic and clinical data, but have not generally been utilized in that manner because of the vast complexities and incompatibilities that characterizes the current medical system.

One data warehousing solution that is specific to health care is the Common Health Framework (CHF) developed by the Connecting For Health, a consortium sponsored by the Merkle and Robert Wood Johnson Foundations. Their 2005 report is published at http://www.connectingfor_health.org/assets/reports/linking_report_2_2005.pdf, which along with and any other referenced patents and applications are incorporated herein by reference in their entirety. Where a definition or use of a term in a reference, which is incorporated by reference herein is inconsistent or contrary to the definition of that term provided herein, the definition of that term provided herein applies and the definition of that term in the reference does not apply.

According to the Framework, a central store contains only (a) patient identification information and (b) links to records in local databases. The idea is that the local databases can best maintain security and confidentiality of their own data, but queries can still be run against the central store for individual patients. Unfortunately, use of patient identification information as the sole portals through which one can access data means that the system provides only very limited and very difficult access to epidemiological data. For example, anyone wanting to run a correlation of particular AIDS treatments against side effects would first need to identify which patients have been diagnosed with AIDS. And there is no provision with the Framework for discovering which patients have that diagnosis. Thus, although the Framework can be used to great advantage to schedule individual patients appointments with clinicians, the Framework is unable to answer questions directed to how many (or what percentage of) patients having a given diagnosis missed their appointments during the last month. Consequently, there is still a need for a system that combines demographic, clinical, and other practice-related data from multiple independent data stores, and that can be conveniently mined for correlations by clinicians having only ordinary computer skills.

SUMMARY OF THE INVENTION

The present invention provides systems and methods in which data is combined from multiple independent data stores, and is then queried using a data correlation engine.

Contemplated engines preferably keep track of previously run correlations, and then makes those correlations available to clinicians for their own use. For example, a preferred system might provide a listing of correlations run by other clinicians in a particular medical specialty, or a particular community, whether geographic or otherwise. In another example, a preferred system might provide a listing of correlations sorted by popularity, so that the most frequently accessed correlations appear near the top of the list. In any case a clinician could simply view the list, and check off which correlations he/she would like to have run for his/her practice, or practice community.

In another aspect it is contemplated that the correlations engine could be set to run different ones of the correlations according to different schedules; some correlations being run daily, with others being run weekly, monthly or otherwise.

In yet another aspect it is contemplated that output of the correlations engine could be presented to the requester (or some other entity) according to a user-selected format, perhaps using a presentation interface. For example, one clinician may choose to view a single display screen the lists results of all of his/her selected queries. Another clinician may choose to have results sent daily in an email message. Still other clinicians might choose to receive results for given queries only in exceptional cases, and thereby use the system as a form of alert. For example, a physician may want to know if the number of no-shows for appointments in any given month rises more than 15% above a running average, or whenever a patient being treated for a given condition reports a particular set of side effects.

Various objects, features, aspects and advantages of the inventive subject matter will become more apparent from the following detailed description of preferred embodiments, along with the accompanying drawings in which like numerals represent like components.

DETAILED DESCRIPTION

Figure 1:
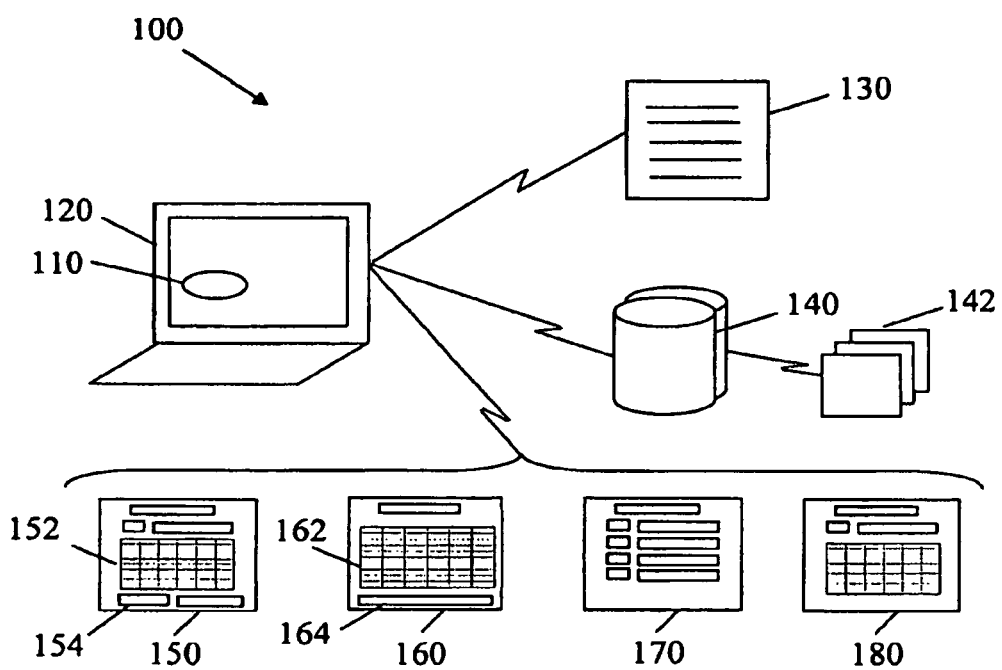
FIG. 1 is a schematic of a correlation engine according to aspects of the present invention.

In FIG. 1, a data correlation engine 100 generally includes software 110 running on computer 120, a set of correlations 130 that can be run against one or more databases 140 that stores clinical data, and 150 selection and presentation interfaces 150, 160. FIG. 1 should be interpreted according to the following description.

Software 110 can be any suitable software, written in any language or combinations of languages. All suitable operating platforms and/or environments are contemplated, including for example web applications. These are all generically represented by computer 120.

Database(s) 140 can be of any suitable size, format, organization, and so forth. The clinical data contained in the database(s) can advantageously be derived from medical care facilities 142 located in one, two, three or more three different countries.

Selection interface 150 preferably includes fields 152 through which a first user can select a non-trivial proper sub-set of the correlations to be automatically run against the database to provide a set of alerts, and through which the user can add new correlation query to the set of correlations, and second, third and other users can then select the new correlation as part of their own sets of selected correlations. The correlations are preferably characterized according to at least one of medical specialty, popularity, and community. The selection interface also preferably includes at least one of an opt-in and an opt-out choice 154. The un-numbered fields in each of the interfaces should be interpreted generically as indicating that all suitable combinations of fields and data are contemplated.

The presentation interface 160 preferably includes alerts 162 as discussed elsewhere herein, a natural language interface 164 through which the first user can select the sub-set of the correlations.

It is especially contemplated that a second user could use the selection interface 150 to select a second non-trivial proper sub-set of the correlations 130 to be automatically run against a second database 140 to provide a second set of alerts.

Figure 2:
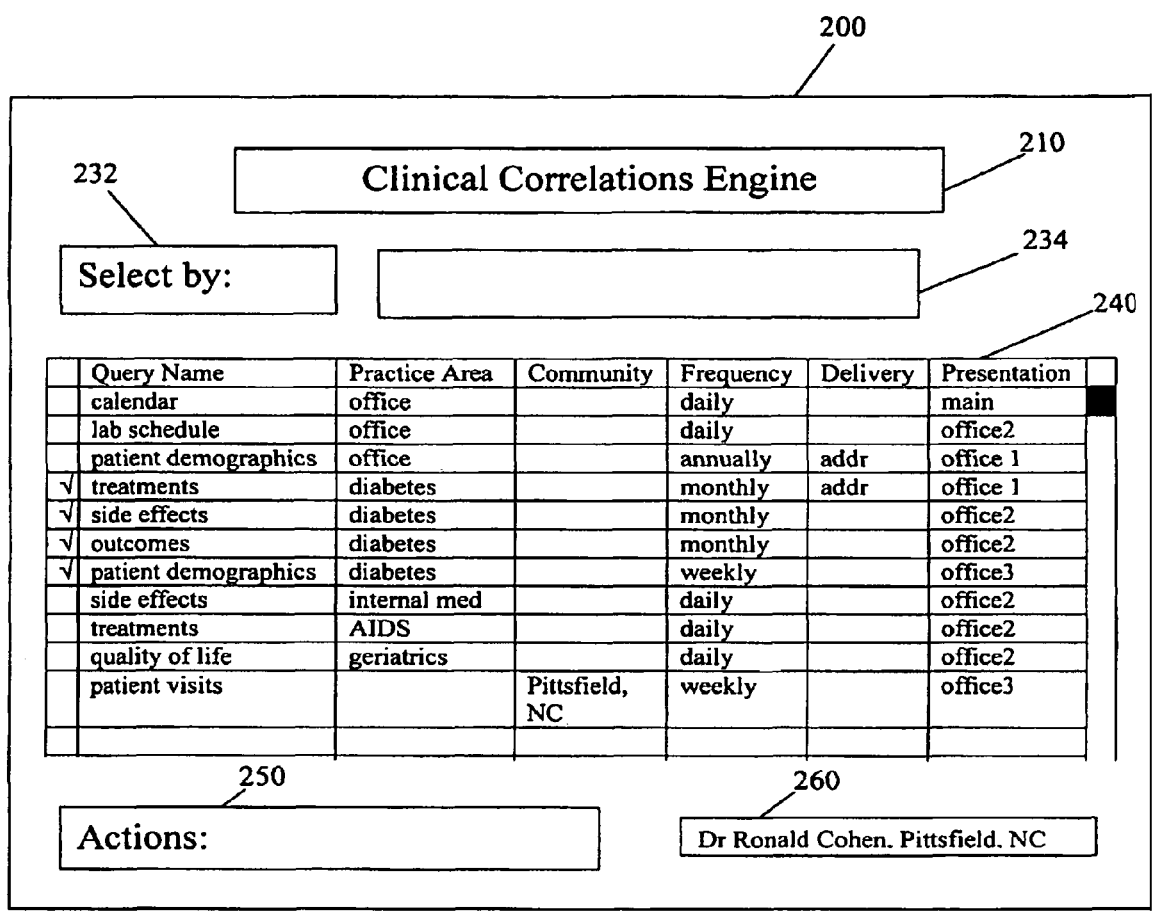
FIG. 2 is a sample interface for a data correlations engine.

Selection and presentation interfaces 150, 160 are preferably combined into a single interface, such as that shown in FIG. 2, which preferably includes a web based interface. These and all other interfaces can be customized by the user.

The data correlation engine 100 also preferably includes a periodicity interface 170 through which the user can select periodicity at which at least some of the alerts will be run, and a an additional interface 180 through which the user can add a new correlation to the set of correlations, and wherein the second user can select the new correlation as falling within the second sub-set of the correlations.

The data correlation engine 100 also preferably includes a translator (as part of software 110) that translates elements of the individual ones of the set of correlations into a language other than that in which the elements were originally stored.

FIG. 2 depicts a combined selections and presentation interface through which a user can select or de-select designate queries to be run, and can choose running characteristics such as frequency, delivery, and presentation.

In this particular embodiment an interface 200, typically operable on a standard display over the Internet, generally includes two selection fields 232, 234, a table 240 that lists queries, an actions field 250, and an user identification field 260. Selection field 232 likely includes a drop-down menu (not shown) for a user to select among various choices for data to include in the table 240. Currently contemplated choices include "My Queries", "Practice Area", "Community", "Recent Additions", "Popular Queries", and so forth. The related selection field 234 likely also includes a drop-down menu, with choices dependent upon the selection made for field 232. For example, if the user selected "Practice Area" for field 232, the choices in field 234 might be "General Medicine", "Pediatrics", "Coronary Care", "Emergency Medicine", "Urology", "Obstetrics", etc. If the user selected "Community" for field 232, the choices in field 234 might be "AIDS", "Diabetes" or some other particular disease, perhaps the name of a city, or perhaps some other association or affinity group such a church or religion, or perhaps "Managed Care". There is a vertical slider on the right. Horizontal sliders and other common navigational aids are also contemplated.

Table 240 lists names of queries that are previously stored on the system. Details of the queries can be viewed at some other interface, and presumably new queries could be added there as well. In this particular embodiment the table 240 shows metadata relating to the query, namely "Practice Area", "Community", "Frequency", "Delivery", and "Presentation". "Practice Area" and "Community" should correspond with choices in the selection fields 232, 234. Frequency identifies how frequently the query will run for this particular user. "Delivery" contains an address for delivery of the query results, and could for example include a fax number, email address, and so forth. "Presentation" contains names of displays to which the particular results would be exported. Thus, in this example output for some of the queries would go to a display called "office1" and output for others of the queries would go to a display called "office2".

The first column of table 240 contains cells that can be checked or unchecked with respect to action 250. Action 250 can be any suitable action, such as "add", "delete", "hide", "unhide" and so forth.

Various sorts are also contemplated, so that for example, the rows of the table (or perhaps the checked rows) can be sorted by any of columns.

Of course, users can also create and add new queries, which can then be made available to other users. In that way the database of queries will grow, with physicians and others being able to take advantage of interesting queries created by others. Adding new queries can be accomplished in any suitable manner, and is accessed in this example by clicking on the <add new query> button in the last row of the table.

Although the text of FIG. 1 is in English, it is also contemplated that a translator can provide interfaces in one or more other languages. Still further, a translator can be used to translate one or more elements (field names and verbs) used in the correlation queries. It is also contemplated that users can create and enter correlation queries using a natural language interface. All suitable databases are contemplated for storing the clinical data against which correlation queries can be run. One especially preferred embodiment federates data from, or at least provides links to, data held by numerous independent medical facilities, which can include hospitals, practice groups, sole practitioners, government data bases, and so forth. It is especially contemplated that the datastores from which the clinical data is copied, or to which the database points, can include datastores in many different states or even many different countries.

It should be apparent to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps could be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A data correlation engine that uses a computer to run a set of queries against a database that electronically stores clinical data, comprising:

a stored set of queries that had been previously created by a first user and run against the database, wherein each individual query within the set is associated with a first parameterized value corresponding to a first category and a second parameterized value corresponding to a second category;

a filtering interface configured to (1) receive a category selection from a second user, (2) automatically present to the second user a plurality of parameterized values corresponding to the selected category, (3) receive from the second user a selection of a parameterized value from the plurality of parameterized values, and (4) retrieve a non-trivial proper sub-set of the queries based on the selected category and the selected parameterized value;

a query selection interface through which the second user can select one or more queries from the retrieved sub-set of queries to be automatically run against the database according to a periodicity schedule to provide a set of exceptional case alerts;

a presentation interface through which the second user can select a presentation aspect of how at least one of the exceptional case alerts will be presented to the second user; and a correlation module configured to (1) run the selected one or more queries against the database to produce a first value, (2) perform a comparison operation between the produced first value and a second pre-determined value to generate a difference value, and (3) present an exceptional case alert to the second user according to the selected presentation aspect only when the difference value indicates are exceptional case.

2. The engine of claim 1, wherein the selection interface includes at least one of an opt-in and an opt-out choice.

3. The engine of claim 1, further comprising a periodicity interface through which the user can select periodicity at which at least some of the alerts will be run.

4. The engine of claim 1, wherein at least one of the filtering and selection interfaces includes a web based interface.

5. The engine of claim 1, wherein the filtering interface is configured to (1) receive a category selection from a third user, (2) automatically present to the third user a plurality of parameterized values corresponding to the selected category, (3) receive from the third user a selection of a parameterized value from the plurality of parameterized values, and (4) retrieve a non-trivial proper sub-set of the queries based on the selected category and the selected parameterized value to run against a second database to provide a second set of alerts.

6. The engine of claim 1, further comprising an additional interface through which the second user can add a new query to the set of queries, and wherein the second user can select the new query as falling within the sub-set of the queries.

7. The engine of claim 1, wherein the selection interface is customizable by the user.

8. The engine of claim 1, wherein the first user can add a new query to the set of queries, and second, third and other users can then select the new query as part of their own sets of selected queries.

9. The engine of claim 1, further comprising a translator that translates elements of the stored queries into a language other than that in which the elements were originally stored.

10. The engine of claim 1, wherein the filtering interface is configured to receive the category selection as a natural language input from a second user.

11. The engine of claim 1, wherein the clinical data is derived from medical care facilities located in at least three different countries.

12. The engine of claim 1, wherein the category is medical specialty.

13. The engine of claim 12, wherein the plurality of parameterized values includes at least one of general medicine, pediatrics, coronary care, emergency medicine, urology, and obstetrics.

14. The engine of claim 1, wherein the category is community.

15. The engine of claim 14, wherein the plurality of parameterized values includes at least one of AIDS and diabetes.

* * * * *